United States Patent [19]

Nader

[11] Patent Number: 5,194,652

[45] Date of Patent: Mar. 16, 1993

[54] OXIDATION-RESISTANT CYCLOPHOSPHAZENE FLUID INCLUDING TRIARYLPHOSPHINE OR PHOSPHINE OXIDE

[75] Inventor: Bassam S. Nader, Midland, Mich.

[73] Assignee: The Dow Chemical Company, Midland, Mich.

[21] Appl. No.: 891,378

[22] Filed: May 29, 1992

[51] Int. Cl.$^5$ .................... C07F 9/6593; C07F 9/6581
[52] U.S. Cl. ..................................................... 558/80
[58] Field of Search ...................... 558/80; 568/13, 15, 568/16

[56] References Cited

U.S. PATENT DOCUMENTS 5,099,055  3/1992  Kar et al. ............................... 558/80

Primary Examiner—Mary C. Lee
Assistant Examiner—Michael G. Ambrose

[57] ABSTRACT

The oxidation resistance of a cyclophosphazene-based fluid (such as a lubricant or a hydraulic fluid) can be improved by the addition to the fluid of an oxidation-inhibiting amount of an aryl phosphine or phosphine oxide. The aryl phosphine or phosphine oxide is preferably present in an amount of about 0.01 to about 5 percent by weight. The aryl phosphine or phosphine oxide can be (a) a symmetric triarylphosphine of formula $R_3P$, wherein R is 4-trifluoromethyl phenyl, 3-trifluoromethyl phenyl, 3-trifluoromethoxy phenyl, 3-(3-trifluoromethylphenoxy) phenyl, 3-(perfluoro-2, 5-dimethyl-3, 6-dioxanonyl) phenyl or 1-naphthyl; (b) an oxide of any of these symmetric triarylphosphines; or (c) 1, 3-bis(diphenylphosphino) benzene. The cyclophosphazene fluid component is preferably a (fluorinated phenoxy) (3-perfluoroalkylphenoxy)-cyclic phosphazene of the general formula (I):

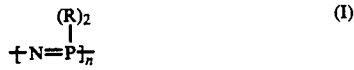

wherein n is 3 to 7, inclusive; wherein R is individually in each occurrence fluorinated phenoxy or 3-perfluoroalkylphenoxy; and wherein the ratio of fluorinated phenoxy to 3-perfluoroalkylphenoxy is about 1:5 to 1:1 inclusive. Although useful as antioxidants in other fluids such as polyphenyl ethers, perfluorinated aliphatic polyethers and polyol esters, the antioxidant activity of the defined aryl phosphines and phosphine oxides in cyclophosphazene fluids is unexpected because of the significant difference in the pathways of oxidative degradation between the cyclophosphazenes and these other fluids.

11 Claims, No Drawings

OXIDATION-RESISTANT CYCLOPHOSPHAZENE FLUID INCLUDING TRIARYLPHOSPHINE OR PHOSPHINE OXIDE

TECHNICAL FIELD

The present invention relates to the inhibition of oxidation in functional fluids such as lubricants or hydraulic fluids, and more particularly to the inhibition of oxidation in cyclophosphazene fluids.

BACKGROUND OF THE INVENTION

Cyclophosphazene fluids are known to be useful as lubricants, hydraulic fluids, fuel additives, flame retardants, and for a variety of other purposes as well. The polyfluoro-substituted cyclophosphazenes, especially the polyfluoro-substituted cyclotriphosphazenes, appear to be a particularly useful group of cyclophosphazenes. As a class, the cyclophosphazenes appear to have significant potential as high temperature lubricants or hydraulic fluids, that is, at service temperatures in excess of 250° C. Applications at these high temperatures include use in jet aircraft, turbine and diesel engines.

Unfortunately, when employed at high temperatures in ambient atmospheres, the cyclophosphazenes can oxidize, and their utility thereby suffer. Oxidation of the cyclophosphazenes can cause the formation of solid deposits in them, can change their viscosities or lubricities, and can increase their corrosivity (that is, increase their acid number). U.S. Pat. No. 4,724,264 (Feb. 9, 1988, Nakacho et al.) discloses an attempt to avoid the problem of oxidation by employing particular substituents on the cyclophosphazene which render it less subject to oxidation. However, the selection of these particular substituents defines and therefore limits the circumstances under which the substituted cyclophosphazene fluid may be used.

At least one attempt has been made to protect cyclophosphazene fluids from oxidation by adding an antioxidant to them. More particularly, U.S. Pat. No. 3,313,731 (Apr. 11, 1967, Dolle, Jr. et al) discloses the use of perfluorinated aryltin compounds as antioxidants in cyclic triphosphonitriles (cyclotriphosphazenes) and polyfluoroalkoxy-substituted triazines. Of course, the triaryltin compounds are now known to be among the leading high temperature antioxidant additives for other conventional fluids, such as the polyphenyl ether fluids.

The '731 patent discloses good utility for the perfluorinated aryltins in the triazine fluids. However, the data given in the patent also disclose that less success was enjoyed when the aryltins were employed in the cyclotriphosphazenes. Comparative Sample A disclosed in Example below further demonstrates that the perfluorinated triaryltins are less than satisfactory as antioxidants in cyclophosphazenes, because the protection they provide is inadequate for high temperature uses of the cyclophosphazenes. Indeed, the use of aryltin compounds has often been found to be detrimental to the properties of the cyclophosphazenes.

Other antioxidant materials are of course known to be useful in other fluids. For example, it has long been known to employ triarylphosphines and phosphine oxides as antioxidant or anticorrosive additives in perfluorinated aliphatic polyether or polyol ester lubricants. The triarylphosphines and other known antioxidants, however, would be expected to lack utility in cyclophosphazene fluids for a variety of reasons. The known antioxidants are often immiscible with cyclophosphazene fluids. Known antioxidants often have a high volatility, such that they do not remain in cyclophosphazene fluids very long when employed at high temperatures. Many known antioxidants also possess low thermal stability, again, rendering them less than useful for high temperature applications. Some antioxidants have unacceptable decomposition products, interfering with the desired function of cyclophosphazene fluids. Similarly, some known antioxidants have an unacceptable coefficient of viscosity at high temperatures, that is, they interfere with the viscosity or lubricity of cyclophosphazene fluids. Indeed, many known antioxidants have narrow liquid ranges, that is, they have a high pour point and a low boiling point.

Perhaps the most significant reason why the antioxidants useful in other fluids are not expected to be useful in cyclophosphazene fluids is that cyclophosphazene fluids have an oxidative degradation mechanism which is substantially different from those of conventional fluids or lubricants, such as the polyphenyl ethers, the polyol esters and the perfluorinated aliphatic polyethers. Put simply, if the known antioxidants work by interfering with one step or another in the oxidative pathway associated with the oxidation of a conventional fluid, and if the oxidative pathway for cyclophosphazenes lacks such a step, the conventional antioxidants couldn't be expected to interfere in the oxidative pathway for the cyclophosphazenes.

As a more particular example, it is known that antioxidants for polyphenyl ether fluids function by the formation of a free radical, which reacts in a series of reactions with compounds such as the phenols, in order to form more stable radicals. As explained in more detail in "High-Temperature Stabilization of Polyphenyl Ethers By Inorganic Salts," Ravner et al., 15 ASLE Transactions 45–53 (1971), the antioxidants act as electron sinks during the free radical reaction, and the overall oxidation rate of the base fluid is thus curtailed by the antioxidants. The paragraph bridging pages 50 and 51 of the article notes a variety of potential reaction pathways in the neat ether fluids. The article, and in particular that paragraph, are expressly incorporated by reference herein.

In contrast, oxidation of cyclophosphazene fluids does not entail a free radical reaction. Rather, it appears that cyclophosphazenes oxidize by a cationic mechanism, such that the major oxidation products are arylphosphate esters, arylphosphate ester acids, arylphosphate ester amides, and arylphosphate ester nitriles. The complete oxidation mechanism of the cyclophosphazenes is not yet understood, and research into the mechanism is continuing. However, the cationic mechanism for oxidation of cyclophosphazenes may proceed as follows:

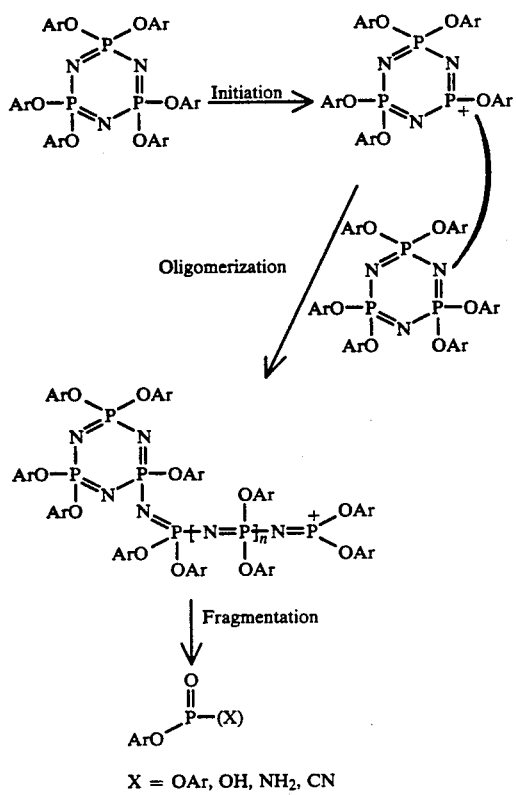

X = OAr, OH, NH$_2$, CN

Whatever the details of the true mechanism may be, it is clear that conventional antioxidants such as organometallic salts (for example, triaryltins), being electron sinks, could not reasonably be expected to interfere in the oxidation of the cyclophosphazenes, since their oxidation entails a cationic mechanism. Despite the resulting expectation that conventional antioxidants are not useful in cyclophosphazenes, it would still be highly desirable to find materials which could successfully function as antioxidants in cyclophosphazenes.

It is therefore an object of the present invention to provide a cyclophosphazene fluid with an effective antioxidant, so as to stabilize the cyclophosphazene fluid against oxidation when used in ambient air at the high operating temperatures encountered in jet aircraft, turbine and diesel engines.

It is another object of the present invention to provide cyclophosphazene fluids with antioxidants having relatively low volatility, high thermal stability, tolerable decomposition products and a wide liquid range, that is, a low pour point and a high boiling point.

SUMMARY OF THE INVENTION

The present Applicant has discovered, contrary to the expectation one skilled in the art would have from the unsatisfactory results obtained with aryltin and other conventional antioxidants, that a defined group of aryl phosphines and phosphine oxides function very well as antioxidants in cyclophosphazene fluids, particularly in the polyfluoro-substituted cyclotriphosphazenes. The present Applicant has tested a number of other aryl phosphines and phosphine oxides, and found them to be unacceptable for many of the reasons noted above, with respect to other antioxidants. The apparent lack of any homologous structure between the useful phosphines, in comparison to those found not to be useful, serves as further proof that the utility of the defined phosphines and phosphine oxides is unexpected.

Thus, in a first aspect, the present invention is directed to an oxidation-resistant cyclophosphazene fluid composition, comprising: a cyclophosphazene fluid component; and an oxidation inhibiting amount of an aryl phosphine or phosphine oxide selected from the group consisting of: (a) symmetric triarylphosphines of formula R$_3$P, wherein R is selected from the group consisting of 4-trifluoromethyl phenyl, 3-trifluoromethyl phenyl, 3-trifluoromethoxy phenyl, 3-(3-trifluoromethylphenoxy) phenyl, 3-(perfluoro-2, 5-dimethyl-3, 6-dioxanonyl) phenyl, and 1-naphthyl; (b) oxides of these symmetric triarylphosphines; and (c) 1, 3-bis(diphenylphosphino) benzene. The cyclophosphazene fluid composition enjoys its greatest utility as a hydraulic fluid or as a lubricant for metal parts at service temperatures in excess of 250° C., and the invention is also directed to a method of lubrication comprising supplying to such metal parts the oxidation-resistant cyclophosphazene fluid composition defined above.

In a related aspect, the oxidation-resistant fluid composition includes about 0.01 to about 5 percent by weight of the defined aryl phosphine or phosphine oxide.

In another related aspect, the cyclophosphazene fluid component of the composition is of the general formula (I):

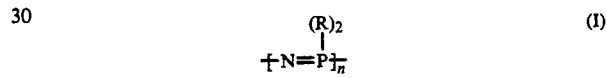

wherein n is 3 to 7, inclusive; wherein R is individually in each occurrence fluorinated phenoxy or 3-perfluoroalkylphenoxy; and wherein the ratio of fluorinated phenoxy to 3-perfluoroalkylphenoxy is about 1:5 to 1:1, inclusive.

The present invention is particularly advantageous in that the defined group of aryl phosphines and phosphine oxides provide superior oxidation resistance to cyclophosphazene fluids, in comparison to the only other antioxidant (triaryltin) known to have some utility in cyclophosphazenes. The present invention thus allows the cyclophosphazenes to be employed at temperatures above 250° C., in accordance with their previously-unrealized potential.

DETAILED DESCRIPTION OF THE INVENTION

As indicated above, the oxidation-resistant cyclophosphazene fluid composition of the present invention comprises a cyclophosphazene fluid component and an oxidation-inhibiting amount of a defined aryl phosphine or phosphine oxide. It is expected that the cyclophosphazene fluid component may be any cyclophosphazene which is liquid under the intended temperatures and the pressures of use, without regard to the nature of the substituents on it. Of course, a cyclophosphazene useful as the cyclophosphazene fluid component of the present invention must be of a type such that its oxidation is inhibited by the defined aryl phosphines or phosphine oxides of the present invention. Any cyclophosphazene undergoing oxidation via a cationic mechanism should find its oxidation inhibited by the defined aryl phosphines or phosphine oxides, and accordingly should be useful in the practice of the present invention. The easiest way to determine the suitability in any particular cyclophosphazene as a cyclophosphazene fluid component of the present invention is simply to add one of the defined aryl phosphine or phosphine oxides to it, and compare its oxidation resistance to a sample of it lacking the aryl phosphine or phosphine oxide. A variety of tests are well known for determining oxidation resistance; two preferred tests are described in the Examples below.

Cyclophosphazenes preferred as the cyclophosphazene fluid component in the present invention are trimeric oligomers, that is, containing three —N=P—units (the cyclotriphosphazenes). However, as a practical matter, the presently known methods of producing cyclophosphazenes typically yield materials containing at least minor amounts of higher oligomers. Thus, more preferably, cyclophosphazenes useful as the cyclophosphazene fluid component in the present invention contain at least about 90 percent or more of trimeric oligomers, and may contain up to about 10 percent of tetrameric and higher oligomers. Cyclophosphazenes containing greater proportions of tetrameric and higher ogliomers are still contemplated as useful in the practice of the present invention, however.

Cyclophosphazenes preferred for use as the cyclophosphazene fluid component in the present invention possess fluorinated aliphatic and/or fluorinated alkyl aliphatic substituent groups, particularly groups containing oxygen. The particularly preferred cyclophosphazenes correspond to the general formula (I):

(I)

wherein n is 3 through 7 and R is individually in each occurrence fluorinated phenoxy or 3-perfluoroalkylphenoxy, with the proviso that the ratio of fluorinated phenoxy to 3-perfluoralkylphenoxy ranges from about 1:5 to about 1:1.

The fluorinated phenoxy moieties can contain from one to five fluorine atoms. It is preferred that the fluorinated phenoxy moiety contains one fluorine atom and that the fluorine atom is ortho-, meta-, or para- to the oxygen atom of the phenoxy moiety. The perfluoroalkyl group of the meta-perfluoroalkylphenoxy is preferably a lower perfluoroalkyl group having from one to about five carbon atoms and is most preferably a trifluoromethyl group. The preferred fluorinated phenoxy moiety is selected from the group consisting of 3-(3-trifluoromethylphenoxy)phenol and bis(3-phenoxyphenol).

The ratio of fluorinated phenoxy to perfluoroalkylphenoxy substituents ranges from about 1:5 to about 1:1. It is preferred that the ratio ranges from about 1:2 to about 1:1. It is more preferred that the ratio is about 1:2. While the cyclophosphazene compounds are described as single molecules having specified substituents present in a stated ratio, it will be realized by one skilled in the art that the compounds actually exist as statistical mixtures of molecules. Some of these molecules will have higher or lower ratios. However, the phosphazines will, within these statistical mixtures, have substituents present at the specified ratios.

The following are non-limiting examples of the cyclophosphazenes wherein the m-perfluoroalkyl phenoxy substituent is a 3-fluoromethyl phenoxy moiety. These examples include 2,2,4,4,6,6-di(4-fluorophenoxy)tetra(3-trifluoromethylphenoxy)-1,3,5-triaza-2,4,6-triphosphorine, 2,2,4,4,6,6-di(3-fluorophenoxy)tetra(3trifluoromethylphenoxy-1,3,5-triaza-2,4,6-triphosphorine, 2,2,4,4,6,6-di(2-fluorophenoxy)tetra(3-trifluoromethylphenoxy)-1,3,5-triaza-2,4,6triphosphorine, 2,2,4,4,6,6-tri(2-fluorophenoxy)tri(3-trifluoromethylphenoxy)-1,3,5-triaza-2,4,6triphosphorine, 2,2,4,4,6,6-tri(3-fluorophenoxy)tri(3-trifluoromethylphenoxy)-1,3,5-triaza-2,4,6-triphosphorine, 2,2,4,4,6,6-tri(4-fluorophenoxy)tri(3-trifluoromethylphenoxy)-1,3,5-triaza-2,4,6-triphosphorine, 2,2,4,4,6,6,8,8-tri(4fluorophenoxy)penta(3-trifluoromethylphenoxy)-1,3,5,7-tetraza-2,4,6,8-tetraphosphorine, 2,2,4,4,6,6,8,8-tri(3fluorophenoxy)penta(3-trifluoromethylphenoxy)-1,3,5,7-tetraza-2,4,6,8-tetraphosphorine, 2,2,4,4,6,6,8,8tetra(4-fluorophenoxy)tetra(3-trifluoromethylphenoxy)1,3,5,7-tetra-2,4,6,8-tetraphosphorine, 2,2,4,4,6,6,8,8-2.57(3-fluorophenoxy)-5.43(3-trifluoromethylphenoxy)-1,3,5,7-tetraza-2,4,6,8-tetraphosphorine, 2,2,4,4,6,6,8,8-2.57(3-fluorophenoxy)-5.43(3-trifluoromethylphenoxy)-1,3,5,7-tetraza-2,4,6,8tetraphorine, 2,2,4,4,6,6,8,8-2.57(4-fluorophenoxy)-5.43(3-trifluoromethylphenoxy)-1,3,5,7-tetraza-2,4,6,8-tetraphorine, and mixtures thereof. In a preferred embodiment, the cyclophosphazene is either 2,2,4,4,6,6-di(3-fluorophenoxy)tetra(3-trifluoromethylphenoxy)-1,3,5-triaza-2,4,6-triphosphorine, 2,2,4,4,6,6-di(4fluorophenoxy)tetra(3-trifluoromethylphenoxy)-1,3,5-triaza-2,4,6-triphosphorine, or mixtures thereof.

The cyclophosphazene fluids may be prepared in a one-pot, two-stage reaction. As an example, in the first stage, a fluorinated phenol and a perfluoroalkylphenol are placed into a flask with a solvent. An alkali metal hydroxide is added and the mixture is allowed to reflux followed by the waters of reaction being removed. The mixture is then allowed to cool, a halogenated cyclophosphazene is added, and then the new mixture is again refluxed. The product is recovered using conventional recovery techniques. The fluorinated phenol, perfluoroalkylphenol and halogenated cyclophosphazene starting materials are commercially available or may be prepared using conventional techniques.

In the preparation of the cyclophosphazene fluids, the fluorinated phenol, the perfluoroalkylphenol and the halogenated phosphazine reactants are used in amounts sufficient to insure that the fluorinated phenol and perfluoroalkylphenol are present in a ratio of from about 1:1 to about 1:2 and the fluorinated phenol and perfluoroalkylphenol substantially replace the halogens on the phosphazine ring. For example, when the cyclophosphazene is predominantly a trimer such as 2,2,4,4,6,6-hexachloro-1,3,5-triaza-2,4,6-triphosphorine, it is preferred to use at least about two moles of fluorinated phenol and at least about four moles of perfluoroalkylphenol per mole of 2,2,4,4,6,6-hexachloro-1,3,5-triaza-2,4,6-triphosphorine. When the phosphazine is a tetramer, it is preferred to use at least about 2.6 moles of fluorinated phenol and at least about 5.4 moles of perfluoroalkylphenol per mole of 2,2,4,4,6,6,8,8-octachloro-1,3,5,7-tetraza-2,4,6,8-tetraphosphorine. It is preferred to use a slight stoichiometric excess each of fluorinated phenol and perfluoroalkylphenol to insure complete reaction.

The particularly preferred cyclophosphazenes described above, and their methods of preparation, are disclosed in more detail in U.S. Pat. No. 5,015,405 (March, 1991, Kar et al.), which is expressly incorporated by reference herein in its entirety. Particular reference is made to Examples 1 through 3, at column 4, line 12 through column 5, line 12 of the patent specification.

Again, as indicated above, these preferred cyclophosphazenes are employed in combination with an oxidation-inhibiting amount of a defined aryl phosphine or phosphine oxide. The aryl phosphines and phosphine oxides useful in the practice of the present invention include 1,3-bis(diphenylphosphino)benzene and certain symmetrical triarylphosphines and their oxides. The symmetric trarylphosphines are of the general formula $R_3P$, wherein R is 4-trifluoromethyl phenyl, 3-trifluoromethyl phenyl, 3-trifluoromethoxy phenyl, 3-(3-trifluoromethylphenoxy) phenyl, 3-(perfluoro-2,5-dimethyl-3,6-dioxanonyl) phenyl, or 1-naphthyl.

There does not appear to be any specific structure which could be considered to be generic to these materials which by itself would define them as a group. This fact by itself is good evidence that the utility of these materials in the present invention is unsuggested by the prior utility of a variety of triarylphosphines as antioxidants in other fluids. However, the aryl phosphines or phosphine oxides useful in the present invention are either unsubstituted, or have substituents such as perfluoroalkyl, perfluoroalkoxy, or perfluoroalkyl polyether, which are known to be thermally and oxidatively stable. Their substitution patterns are meta- and para-, rather than ortho-.

The fluid composition of the present invention preferably includes about 0.1 to about 5 percent by weight of the defined aryl phosphine or phosphine oxide. Advantageously, the aryl phosphine or phosphine oxide is introduced into the cyclophosphazene fluid component by the use of a compatible solvent, such as methylene chloride. More particularly, the defined aryl phosphine or phosphine oxide can first be suspended or, preferably, dissolved in appropriate quantity of the solvent. The resulting suspension or solution is then mixed with the cyclophosphazene fluid component, and the solvent driven from the resulting mixture. While heat can be employed to remove the solvent, the solvent is preferably removed under vacuum. Any other convenient method of mixing which achieves a uniform dispersion of the aryl phosphine or phosphine oxide in the cyclophosphazene fluid component may also be employed.

Some of the defined aryl phosphines possess only moderate stability in air, and may be subject to a degree of oxidation if allowed to stand in solution for significant time under an ambient atmosphere. Accordingly, it is preferred that the defined aryl phosphines and phosphine oxides be stored neat (that is, without a solvent) under an inert atmosphere, such as nitrogen, after their production and before they are admixed with the cyclophosphazene fluid component.

While all of the defined aryl phosphines and phosphine oxides have an antioxidizing effect in combination with the preferred cyclophosphazene fluid components, the defined aryl phosphines and phosphine oxides do not have identical utility in the practice of the present invention. Most notably, the symmetrical triarylphosphines in which R is 4-trifluoromethyl phenyl, 3-trifluoromethyl phenyl, and 3-trifluoromethoxy phenyl have relatively low molecular weights. These three materials therefore possess a moderate degree of volatility at temperatures on the order of 250° C or above, limiting their utility at higher temperatures. However, these materials still protect the preferred cyclophosphazene fluid components from oxidation at lower temperatures and are expected to extend the life of the preferred cyclophosphazene fluid components. Accordingly, their use still falls within the scope of the present invention.

The aryl phosphines and phosphine oxides useful in the practice of the present invention can be obtained from commercial sources or can be synthesized specifically for the practice of the present invention. For example, commercial tri(1-naphthyl)phosphine (that is, the symmetric triarylphosphine in which R is 1-naphthyl) is useful in the practice of the present invention. If not available on a commercial basis, the aryl phosphines can be synthesized by generating an aryllithium intermediate via metal-halogen exchange of an arylhalide with n-butyllithium, followed by nucleophilic reaction on a phosphorous-halogen bond. It should be noted, however, that this general method usually meets with varying degrees of success. Since the preparation of most of the defined aryl phosphines entails triple displacement on the same phosphorous center (phosphorous trichloride), the method becomes increasingly slow as the displacement reaction progresses, due to a build-up of steric hindrance. The slower the reaction, the more side-products that are obtained. Accordingly, alternative approaches may be desirable for some of the compounds. For example, the aryl phosphine in which R is 3-(3-trifluoromethylphenoxy) phenyl can be synthesized by first generating an aryl Grignard, again followed by nucleophilic displacement on phosphorous trichloride.

The aryl phosphine 1,3-bis(diphenylphosphino) benzene can be prepared by the dilithiation of 1,3-dibromobenzene, followed by reaction with commercially available chlorodiphenylphosphine. However, such a method has been found to give only low yields of product. An alternative approach has been described in the chemical literature which involves the preparation of 1-bromo-3-diphenylphosphinobenzene as an intermediate, followed by lithium-halogen exchange of the intermediate with n-butyllithium, followed by reaction with chlorodiphenylphosphine. The present Applicant has found that, while the 1-bromo-3-diphenylphosphinobenzene can be obtained in quantitative yields, the likelihood of its subsequent conversion to 1,3-bis(diphenylphosphino) benzene may be quite low, and not to be considered successful, presumably due to competitive oxidation to various phosphine oxide side-products.

PREPARATION OF ARYL PHOSPHINES AND PHOSPHINE OXIDES

The preparation of the defined aryl phosphines or phosphine oxides sometimes entailed reactions requiring anhydrous conditions. All reactions requiring anhydrous conditions were therefore performed in oven-dried glassware, which had been cooled under nitrogen. When performed, thin layer chromatography was performed on glass plates precoated with a 0.25 millimeter thickness of silica gel (type GHLF from Analtech, Inc.). Flash chromotography was performed on 230–400 mesh silica gel 60. All reported melting points were determined in open capillary tubes, and are uncorrected. $^1$H-NMR spectra at 300 MHz and uC-NMR spectra at 75.4 MHz were recorded by a Varian VXR300. Tetramethylsilane was employed as an internal standard. Infrared spectra were obtained by use of a Perkin-Elemer 1310 Spectrophotometer. An elemental analysis, when performed, was performed according to standard analytical technique.

PREPARATION OF TRIS(4-TRIFLUOROMETHYLPHENYL)PHOSPHINE (R=4-trifluomethylphenyl)

8 grams of 4-bromobenzotrifluoride were dissolved in 45 milliliters of anhydrous diethylether at 0° C. under a nitrogen atmosphere. 14 milliliters of a 2.5 M solution of n-butyllithium in hexane were then added to the solution via syringe, with stirring, over a 10 minute period. The solution was stirred for 30 minutes at 0° C., and then a solution of 1 milliliter of phosphorous trichloride in 15 milliliters of diethylether was added to the solution dropwise over a 50 minute period. The resulting mixture was warmed to room temperature and stirred for 2½ hours, then quenched with 50 milliliters of a 5 percent solution of hydrochloric acid. The organic phase of the mixture was washed with 50 milliliters of water, followed by 50 milliliters of aqueous sodium chloride solution. The organic phase was then dried over magnesium sulfate, filtered, and concentrated on a rotavap (rotary evaporator). The resulting product was a red-orange oil, yield 5.31 grams. The product included a triarylphosphine oxide side-product. The side-product was removed by precipitation by the addition of hexane, followed by filtration of the side product. The hexane solvent was removed on a rotavap, and the final product was an orange oil which crystallized upon standing. The triarylphosphine product was purified by recrystallization from methanol. The final yield of the triarylphosphine product was 1.95 grams (yield 35%).

The melting point of the triarylphosphine product was 74° to 75° C. The primary mass spectrum peak had an m/z ratio of 466. Infrared (potassium bromide disk) and NMR spectra were consistent with the disclosed structure of the product. The expected elemental analysis of the product was 54.09 carbon and 2.59 percent hydrogen, and 53.99 percent carbon and 2.74 hydrogen were found upon elemental analysis.

The corresponding triarylphosphine oxide had a melting point of 177° to 178° C. and a primary mass spectrum peak of m/z 481. The infrared (potassium bromide disk) and NMR spectra were consistent with the expected structure.

PREPARATION OF TRIS(3(TRIFLUORMETHYLPHENYL)PHOSPHINE (R=3-trifluoromethylphenyl)

10 grams of m-bromobenzotrifluoride were dissolved in anhydrous diethylether under nitrogen at 0° C. 17.8 milliliters of a 2.5 M solution of n-butyllithium in hexane were slowly added to the ether solution via syringe over a 10 minute period, with stirring. The resulting mixture was stirred for an additional 50 minutes at 0° C. 1.29 milliliters of phosphorous trichloride in 20 milliliters of diethylether were then added dropwise to the mixture over a 25 minute period, with stirring. The resulting mixture was stirred for 2 hours at room temperature, and the reaction then quenched with 50 milliliters of a 5 percent aqueous hydrochloric acid solution. 75 milliliters of diethylether were then added, and the organic layer washed with 50 milliliters of water followed by 50 milliliters of aqueous sodium chloride solution. The organic layer was then dried over magnesium sulfate and filtered. The solvent was removed on a rotavap to yield 6.66 grams of a crude product oil. The oil was purified by flash chromatography on a 6 inch by 1 inch inside diameter column packed with flash-grade silica gel. The eluting solvent was hexane. The purified oil was obtained at a 79 percent yield (5.45 grams). The mass spectrum of the product possessed a primary m/z peak at 466. The infrared (neat film) and NMR spectrum of the product were consistent with the expected structure.

PREPARATION OF TRIS(3-TRIFLUOROMETHOXYPHENYL)PHOSPHINE (R=3-trifluoromethoxyphenyl)

5.15 grams of m-bromophenyltrifluoromethyl ether were dissolved in 40 milliliters of anhydrous diethylether under nitrogen at 0° C. 8.5 milliliters of a 2.5 M solution of n-butyllithium were then added dropwise to the ether solution via a syringe, with stirring. The mixture was stirred for an additional 50 minutes at 0° C. 0.62 milliliters of phosphorous trichloride in 10 milliliters of diethylether were then added dropwise to the mixture by syringe over a 10 minute period. The mixture was allowed to warm to room temperature and stirred for 2 hours, after which the reaction was quenched by the addition of 25 milliliters of a 5 percent aqueous solution of hydrochloric acid. 50 milliliters of diethylether were then added to the mixture and the resulting organic layer washed with 25 milliliters of water, then 50 milliliters of aqueous sodium chloride solution. The organic layer was then dried over magnesium sulfate and filtered. The solvent was then removed from the product on a rotavap to leave 2.73 grams of an oil. The product oil was then purified by flash chromotography with hexane on a 6 inch by 1 inch inside diameter column packed with flash-grade silica gel. The resultant product was obtained as a viscous yellow oil at a 38 percent yield (1.41 grams). The product possessed a primary mass spectrum peak at m/z 514, and infrared (neat film) and NMR spectra were consistent with the disclosed structure for the product.

PREPARATION OF TRIS[3-(3-TRIFLUOROMETHYLPHENOXY) PHENYL] phosphine (R=3-(3-trifluoromethylphenoxy) phenyl)

A 1 liter, 3-necked flask was prepared by providing it with a mechanical stirrer, a Dean-Stark trap topped with a condenser and a nitrogen bubbler, and a stopper. The flask was flushed with nitrogen and then charged with 22.4 grams of potassium hydroxide, 64.8 grams of α,α,α-trifluoro-m-cresol and 500 milliliters of toluene. The mixture was stirred and heated at reflux for 2 hours, during which time it was observed that about 6 milliliters of water collected in the trap. 50 milliliters of 3-dibromobenzene and 39.6 grams of cuprous chloride were then added to the reaction mixture, and the mixture heated at reflux for another 18 hours. Analysis of the reaction mixture by capillary gas chromotography disclosed it to contain about 44 percent of 1-bromo-3-(3-trifluoromethyl)phenoxybenzene (determined with reference to a previously prepared and purified sample of verified identity). The crude mixture also contained about 12.5 percent of a product resulting from dialkylation, the rest of the material being the starting materials.

200 milliliters of diethylether were added to the crude reaction mixture, and the mixture then washed successively with two 100 milliliter portions of 5 percent aqueous hydrochloric acid solution, water, and aqueous sodium chloride solution. (The hydrochloric acid was employed to remove any residual copper impurities from the reaction mixture.) The organic mixture was then dried with magnesium sulfate and concentrated on a rotavap to a red, oily residue. The 1-bromo-3-(3-trifluoromethyl)phenoxybenzene was separated from the crude product by fractional distillation. Distillation at 1 millimeter Hg pressure and at 113° to 117° C. provided 47 grams of the product, a 38 percent yield. The desired product was contained in other fractions from the distillation, but no further effort was made to isolate it. The infrared (neat film) and NMR spectra of the product were consistent with the structure 1-bromo-3-(3-trifluoromethyl)phenoxybenzene.

3.2 grams of 1-bromo-3-(3-trifluoromethyl)phenoxybenzene, 0.25 grams of magnesium turnings and 40 milliliters of anhydrous tetrahydrofuran (THF) were stirred under nitrogen and heated at reflux for 6 hours. The mixture was then cooled to 0° C., and 0.29 milliliters of phosphorous trichloride in 10 milliliters of THF added dropwise to the mixture through an addition funnel. The resulting mixture was heated at reflux for 18 hours, then quenched with 20 milliliters of water. 100 milliliters of diethylether were added to the mixture, and the organic layer washed with two 50 milliliter portions of water and a 50 milliliter portion of aqueous sodium chloride solution. The organic layer was then dried over magnesium sulfate, filtered, and concentrated on a rotavap. The procedure yielded a crude oil weighing 2.22 grams. The oil was partially purified by eluting first with hexane, and then with 3 percent ethyl acetate in hexane, via flash chromotography on a 6 inch by 1 inch inside diameter column packed with flash-grade silica gel. The desired product was an oil; although only a crude product, it was determined via high pressure liquid chromatography analysis on a C-18 reverse-phase column to be greater than 70 percent pure. The crude product was further purified by placing the oil on a Kugelrohr apparatus, and heating at 100° to 120° C. under a vacuum of about 1 millimeter Hg for 6 hours. Some 3-(3-trifluoromethyl)phenoxybenzene was found to distill over during heating, which increased the purity of the desired product to about 78 percent, again determined by HPLC analysis. The mass spectrum of the product possessed a primary m/z peak at 742, and the infrared (neat film) and NMR spectra of the product were consistent with the disclosed structure.

PREPARATION OF TRIS[3;
-(PEFLUORO-2,5-DIMETHYL-3,
6-DIOXANONYL) PHENYL]PHOSPHINE
(R=3-(PERFLUORO-2,
5-DIMETHYL-3,6-DIOXANONYL) PHENYL)

26.3 grams of I-bromo-3(perfluoro-2,5-dimethyl-3,6-dioxanonyl) benzene were dissolved in 50 milliliters of diethyl ether at 0° C. under nitrogen. 16 milliliters of a 2.5 M solution of n-butyllithium in hexane were then added to the solution dropwise by a syringe over a 10 minute period, with stirring. The mixture was stirred for an additional 25 minutes at 0° C., then 1.16 milliliters of phosphorous trichloride in 15 milliliters of diethyl ether were added to the solution dropwise over a 15 minute period at 0° C. The resulting mixture was then stirred at room temperature for 16 hours, and quenched with 50 milliliters of a 5 percent aqueous hydrochloric acid solution. 100 milliliters of diethyl ether were then added to the mixture, and the organic layer washed with two 50 milliliter portions of water and 50 milliliters of aqueous sodium chloride solution. The organic layer was then dried over magnesium sulfate and filtered. The solvent was removed on a rotavap to leave 21.2 grams of a dark yellow, oily residue. The product was purified by flash chromotography using hexane as an eluent on a 6 inch by 1 inch inside diameter column packed with flash-grade silica gel. 17.1 grams of a yellow oil were obtained. This yellow oil was purified by distillation on a Kugelrohr apparatus. The desired product was contained in the fraction distilling between 195° and 230° C. at about 1 millimeter Hg pressure. 8.6 grams of the purified oil were obtained, a 37 percent yield. HPLC analysis on a C-18 reverse-phase column disclosed the product to be about 86 percent pure. The infrared (neat film) spectrum of the product was consistent with the disclosed structure.

The product oil was oxidized to the corresponding phosphine oxide by first dissolving 1 gram of the product oil in 20 milliliters of hexane at room temperature, and then adding 0.1 grams of 3-chloroperoxybenzoic acid in 10 milliliters of hexane dropwise over a 40 minute period, with stirring. The mixture was stirred for an additional 18 hours, and a white precipitate formed in the mixture during stirring. The precipitate was removed by filtration, and the filtrate washed with 100 milliliters of a saturated aqueous sodium carbonate solution, to remove any m-chlorobenzoic acid. The organic phase was then dried over magnesium sulfate, filtered, and concentrated on the rotavap. 0.46 grams of a colorless oil were obtained, a 46 percent yield. The infrared (neat film) spectrum of the oil was consistent with the structure of tris[3-(perfluoro-2,5-dimethyl-3,6-dioxanonyl) phenyl] phosphine oxide.

PREPARATION OF
1,3-BIS(DIPHENYLPHOSPHINO)BENZENE

A solution of 15 grams of 1,3-dibromobenzene in 155 milliliters of THF was prepared under nitrogen at −78° C. 93 milliliters of a 2.5 M solution of n-butyllithium in hexane were added to the solution by syringe over a 30 minute period, with stirring. The resulting mixture was then stirred for two hours at −78° C., and 41.7 milliliters of chlorodiphenylphosphine in 150 milliliters of THF added to the mixture over a 30 minute period. The mixture was allowed to warm to room temperature with stirring, and was stirred for 20 hours. The reaction mixture was then quenched with 125 milliliters of a 5 percent aqueous hydrochloric acid solution. 200 milliliters of diethylether were then added, and the organic layer washed with 150 milliliters of water and 100 milliliters of an aqueous sodium chloride solution. The organic layer was then dried over magnesium sulfate, filtered, and concentrated on a rotavap. 45.2 grams of a yellow oil were obtained. The oil was then heated on a Kugelrohr apparatus at 1 millimeter Hg pressure for 12 hours at 150° to 170° C. Gas chromatography-mass spectrometry analysis disclosed the distillate to contain several components, including butyldiphenyl phosphine and 1,3-dibutylbenzene. The pot residue was collected and eluted with hexane by flash chromotography on a 10 inch by 2 inch inside diameter column packed with flash-grade silica gel. 7.48 grams of the desired product were obtained as a yellowish oil, a 26 percent yield. The product was disclosed by HPLC analysis on a C-18 reverse-phase column to be about 86 percent pure. The product possessed a primary mass spectrum peak at m/z of 446, and the infrared (neat film) and NMR spectra of the product were consistent with the disclosed structure.

EXAMPLES

The following examples demonstrate the effectiveness of some of the defined aryl phosphines against oxidation of a particularly preferred cyclophosphazene fluid component, primarily comprising 2,2,4,4,6,6,-di(4-fluorophenoxy)tetra(3-trifluoromethylphenoxy)-1,3,5-triaza-2,4,6-triphosphorine (hereinafter, the "cyclotriphosphazene").

Example 1

20 milliliter samples of the cyclotriphosphazene containing 0.5 percent by weight commercial tri(1-naphthyl) phosphine (Sample 1) or 1 percent tri(3-trifluoromethyl phenyl) tin (Comparative Sample A), as well as a 20 milliliter sample of the cyclotriphosphazene itself (Comparative Sample B), were tested for oxidative stability by a microoxidation/corrosion/acid number test. The test procedure is an adaptation of Federal Test Method Standard 791b, Method 5307.1, "Corrosiveness and Oxidation Stability of Aircraft Turbine-Engine Lubricants." The test was conducted at 290° C. in the absence of metals, with an air flow rate of 1 liter per hour for 24 hours. At the conclusion of the run, each sample was removed from the test tube, and its acid number determined. The following total acid numbers were obtained:

TABLE 1

| Sample | Total Acid Number | | |
|---|---|---|---|
| | before | after | net change |
| 1 | 0.191 | 0.178 | −0.013 |
| Comparative A | 0.081 | 5.590 | +5.460 |
| Comparative B | 0.096 | 2.456 | +2.360 |

These data show that the mixture of the triarylphosphine with the cyclotriphosphazene (Sample possesses a significantly reduced acid number, in comparison to that of the cyclotriphosphazene itself (Comparative Sample B). This demonstrates that oxidative degradation of the cyclotriphosphazene is effectively inhibited by the triarylphosphine. The data also show, in contrast, that the triaryl tin compound (Comparative Sample A) was not merely ineffective as an antioxidant, but appears to have worsened oxidative degradation of the cyclotriphosphazene.

Example 2

Small quantities of Sample 1, Comparative Sample B and a sample containing 0.5 percent of 1,3-bis(diphenylphosphino)benzene in the cyclotriphosphazene (Sample 2) were tested for oxidative stability by differential scanning calorimetry. The test was carried out under 200 psi oxygen pressure. The test instrument rapidly heated each sample in a cell at a rate of 25° C. per minute up to 354° C., and then maintained each sample at that temperature. The heat flow in the cell containing each sample was monitored until a major oxidation exotherm was observed. The time for evolution of the exotherm relates to the oxidative stability of the sample, a shorter time corresponding to a less stable sample, and a longer time corresponding to a more stable sample.

Comparative Sample B required 47.7 minutes until the major oxidation exotherm was evolved, while Sample 1 required 51.4 minutes until the major oxidation exotherm was evolved, and Sample 2 required 55.4 minutes until the major oxidation exotherm was evolved. These data reflect a 7.7 percent improvement in the oxidative stability of Sample 1 over Comparative Sample B, and a 16 percent improvement in the oxidative stability of Sample 2 over Comparative Sample B.

It is clear from Examples 1 and 2 that certain aryl phosphines can provide good oxidation protection to cyclophosphazenes. The particular mechanism by which oxidation is inhibited is not presently known, and the useful aryl phosphines and phosphine oxides do not appear to contain any common structure which would give them their utility in this regard. A number of other aryl phosphines are not suitable for this purpose, however, so the prior use of the triarylphosphines as antioxidants in other fluids cannot be considered to suggest the use of the defined aryl phosphines and phosphine oxides with cyclophosphazene fluids in particular. The substantial differences between the oxidative degradation pathways for the cyclophosphazenes, and those of other fluids in which the aryl phosphines have previously been employed, make it clear that this utility of the defined aryl phosphines and phosphine oxides is unexpected.

Thus, the present invention provides an oxidation-resistant cyclophosphazene fluid composition, one which is particularly adapted for high temperature lubrication and hydraulic applications.

While the invention has been described in terms of specific embodiments, however, it should be appreciated that other embodiments could readily be adapted by those skilled in the art. Accordingly, the scope of the invention is to be considered limited only by the following claims.

What is claimed is:

1. An oxidation-resistant cyclophosphazene fluid composition, comprising:
   a cyclophosphazene fluid component; and
   an oxidation-inhibiting amount of an aryl phosphine or phosphine oxide selected from the group consisting of:
   (a) symmetric triarylphosphines of formula $R_3P$, wherein R is selected from the group consisting of 4-trifluoromethyl phenyl, 3-trifluoromethyl phenyl, 3-trifluoromethoxy phenyl, 3-(3-trifluoromethylphenoxy) phenyl, 3-(perfluoro-2,5-dimethyl-3, 6-dioxanonyl) phenyl, and 1-naphthyl;
   (b) oxides of said symmetric triarylphosphines; and
   (c) 1,3-bis(diphenylphosphino)benzene.

2. The oxidation-resistant fluid composition of claim 1 having about 0.01 to about 5 percent by weight of said arylphosphine or phosphine oxide.

3. The oxidation-resistant fluid composition of claim 1, wherein said cyclophosphazene fluid component is of the general formula

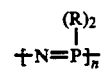

wherein n is 3 to 7, inclusive; wherein R is individually in each occurrence fluorinated phenoxy or 3-perfluoroalkylphenoxy; and wherein the ratio of fluorinated phenoxy to 3-perfluoroalkylphenoxy is about 1:5 to 1:1, inclusive.

4. The oxidation-resistant fluid composition of claim 1, wherein said cyclophosphazene fluid component is 2,2,4,4,6,6-di(4-fluorophenoxy) tetra(3-trifuoromethylphenoxy)-1,3,5-triaza-2,4,6-triphosphorine or 2,2,4,4,6,6-di(3-fluorophenoxy) tetra(3trifluoromethylphenoxy) -1,3,5-triaza-2,4,6triphosphorine.

5. The oxidation-resistant fluid composition of claim 4, wherein said aryl phosphine or phosphine oxide is tris(4-trifluoromethylphenyl) phosphine or phosphine oxide.

6. The oxidation-resistant fluid composition of claim 4, wherein said aryl phosphine or phosphine oxide is tris(3-trifluoromethylphenyl) phosphine or phosphine oxide.

7. The oxidation-resistant fluid composition of claim 4, wherein said aryl phosphine or phosphine oxide is tris(3-trifluoromethoxyphenyl) phosphine or phosphine oxide.

8. The oxidation-resistant fluid composition of claim 4, wherein said aryl phosphine or phosphine oxide is tris[3-(3-trifluoromethylphenoxy)phenyl] phosphine or phosphine oxide.

9. The oxidation-resistant fluid composition of claim 4, wherein said aryl phosphine or phosphine oxide is tris[3-(perfluoro-2,5-dimethyl-3,6-dioxanonyl)phenyl] phosphine or phosphine oxide.

10. The oxidation-resistant fluid composition of claim 4, wherein said aryl phosphine or phosphine oxide is tri(1-naphthyl) phosphine.

11. The oxidation-resistant fluid composition of claim 4, wherein said aryl phosphine or phosphine oxide is 1,3-bis(diphenylphosphino)benzene.

* * * * *